(12) United States Patent
Sakaguchi et al.

(10) Patent No.: US 11,439,634 B2
(45) Date of Patent: Sep. 13, 2022

(54) MEDICAL SKIN EXTERNAL PREPARATION

(71) Applicant: Maruho Co., Ltd., Osaka (JP)

(72) Inventors: Tomoki Sakaguchi, Osaka (JP); Masumi Kawaguchi, Osaka (JP); Ayako Nakamura, Osaka (JP)

(73) Assignee: Maruho Co., Ltd., Osaka (JP)

( * ) Notice: Subject to any disclaimer, the term of this patent is extended or adjusted under 35 U.S.C. 154(b) by 90 days.

(21) Appl. No.: 16/465,559

(22) PCT Filed: Nov. 30, 2017

(86) PCT No.: PCT/JP2017/043180
§ 371 (c)(1),
(2) Date: May 30, 2019

(87) PCT Pub. No.: WO2018/101443
PCT Pub. Date: Jun. 7, 2018

(65) Prior Publication Data
US 2019/0282562 A1  Sep. 19, 2019

(30) Foreign Application Priority Data

Dec. 1, 2016  (JP) .............................. JP2016-234508

(51) Int. Cl.
| A61K 31/4709 | (2006.01) |
| A61K 9/06 | (2006.01) |
| A61K 47/10 | (2017.01) |
| A61K 47/12 | (2006.01) |
| A61P 17/10 | (2006.01) |
| A61P 17/00 | (2006.01) |
| A61P 17/04 | (2006.01) |
| A61P 31/04 | (2006.01) |

(52) U.S. Cl.
CPC ............ *A61K 31/4709* (2013.01); *A61K 9/06* (2013.01); *A61K 47/10* (2013.01); *A61K 47/12* (2013.01); *A61P 17/00* (2018.01); *A61P 17/04* (2018.01); *A61P 17/10* (2018.01); *A61P 31/04* (2018.01)

(58) Field of Classification Search
USPC ......................................... 546/236
See application file for complete search history.

(56) References Cited

U.S. PATENT DOCUMENTS 9,180,200 B2 * 11/2015  Tarrago .................. A61K 47/12

FOREIGN PATENT DOCUMENTS

| JP | 2002-356426 A | 12/2002 |
| JP | 2012-505867 A | 3/2012 |
| JP | 2003-012497 A | 1/2013 |
| JP | 2016-515525 A | 5/2016 |
| WO | 99/51588 A1 | 10/1999 |
| WO | 2007/015453 A1 | 2/2007 |
| WO | 2010/043717 A2 | 4/2010 |
| WO | 2014/145067 A1 | 9/2014 |

\* cited by examiner

*Primary Examiner* — Layla Soroush
(74) *Attorney, Agent, or Firm* — Hodgson Russ LLP

(57) ABSTRACT

An object of the present invention is mainly to provide a medical skin external preparation that is suitable for treating superficial skin infections, in particular, superficial skin infections accompanied by blister or erosion, etc. For example, the present invention can provide a medical skin external preparation containing 1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof as an active ingredient, and an alcohol and/or a fatty acid having 12 or more carbon atoms.

5 Claims, 1 Drawing Sheet

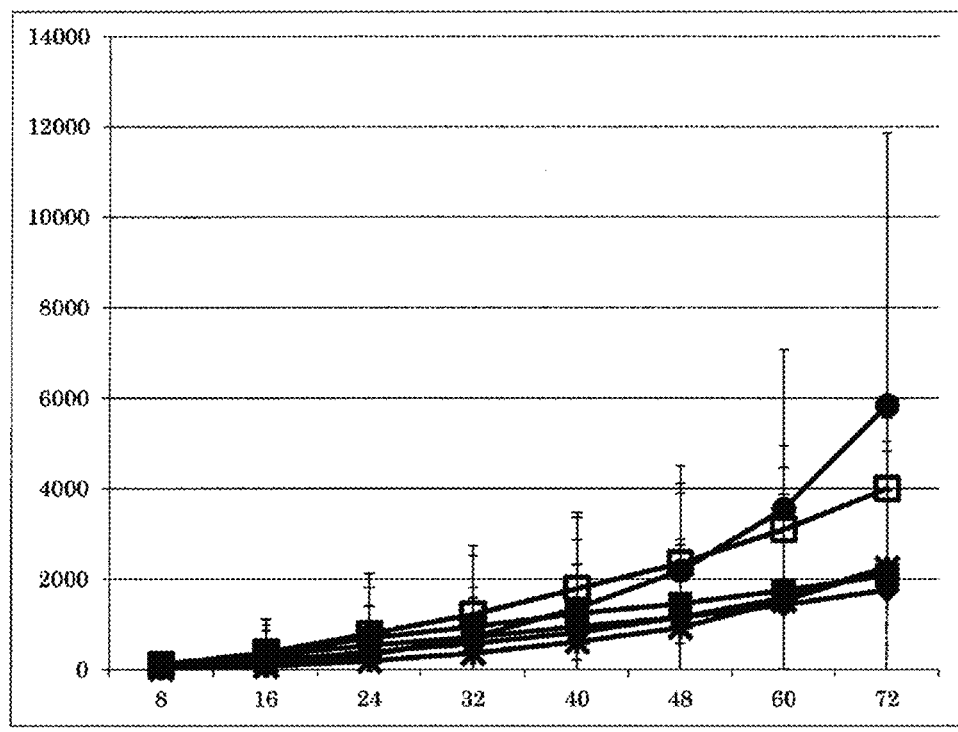

MEDICAL SKIN EXTERNAL PREPARATION

TECHNICAL FIELD

The present invention relates to a medical skin external preparation containing 1-cyclopropyl-8-methyl-7-[5-methyl-6-(methylamino)-3-pyridyl]-4-oxo-1,4-dihydro-3-quinolinecarboxylic acid (hereinafter, referred to as "Compound A") and/or a pharmaceutically acceptable salt thereof as an active ingredient.

BACKGROUND ART

Superficial skin infections, in which various diseases are known such as acne and infectious impetigo, are caused due to multiple factors, and the biggest factor is growth of *Propionibacterium acnes, Staphylococcus* spp. or the like which is a kind of gram positive anaerobic bacteria in the pilosebaceous gland duct.

In a main treating method, a topical antibacterial agent or oral antibacterial agent has been used, or an antibacterial agent has been used such as nadifloxacin, minocycline or roxithromycin. Recently, as a new pharmaceutical product, a formulation containing a Compound A as an active ingredient is on the market (Patent Documents 1 and 2).

PRIOR ART DOCUMENT

Patent Documents

Patent Document 1: WO99/51588
Patent Document 2: WO2007/015453

SUMMARY OF THE INVENTION

Problems to be Solved by the Invention

An object of the present invention is mainly to provide a medical skin external preparation that contains a Compound A as an active ingredient and is suitable for treating superficial skin infections, in particular, superficial skin infections accompanied by blister or erosion, etc.

Means for Solving the Problems

As a result of intensive studies, the present inventors have found that the object can be achieved by adding an alcohol and/or a fatty acid to a medical skin external preparation containing a Compound A and/or a pharmaceutically acceptable salt thereof as an active ingredient, and completed the present invention.

Furthermore, the present inventors have found that a medical skin external preparation having high stability can be provided by controlling the peroxide value of the alcohol and/or the fatty acid to be added to 120 meq/kg or less.

Examples of the present invention may include the followings.

(1) A medical skin external preparation (hereinafter, referred to as "the present inventive medical skin external preparation") contains a Compound A and/or a pharmaceutically acceptable salt thereof as an active ingredient, and an alcohol and/or a fatty acid having 12 or more carbon atoms.

(2) The present inventive medical skin external preparation according to the item 1, further being excellent in stability of the active ingredient.

(3) The present inventive medical skin external preparation according to the item 1 or 2, wherein the content of a degradation product of the active ingredient is 0.5% or less with respect to the active ingredient.

(4) The present inventive medical skin external preparation according to any of the items 1 to 3, wherein the degradation product of the active ingredient is 1-cyclopropyl-3-hydroxy-8-methyl-7-(5-methyl-6-(methylamino)pyridin-3-yl)quinolin-4(1H)-one.

(5) The present inventive medical skin external preparation according to any of the items 1 to 4, wherein the peroxide value of the alcohol and/or the fatty acid is 120 meq/kg or less.

(6) The present inventive medical skin external preparation according to any of the items 1 to 4, wherein the peroxide value of the alcohol and/or the fatty acid is 40 meq/kg or less.

(7) The present inventive medical skin external preparation according to any of the items 1 to 6, wherein the alcohol and/or the fatty acid has 16 to 22 carbon atoms.

(8) The present inventive medical skin external preparation according to any of the items 1 to 6, wherein the alcohol and/or the fatty acid has 18 carbon atoms.

(9) The present inventive medical skin external preparation according to any of the items 1 to 6, wherein the alcohol and/or the fatty acid has an unsaturated carbon bond.

(10) The present inventive medical skin external preparation according to any of the items 1 to 6, wherein the alcohol and/or the fatty acid has a branched chain.

(11) The present inventive medical skin external preparation according to any of the items 1 to 6, wherein the alcohol and/or the fatty acid is lauryl alcohol, hexyldecanol, isostearyl alcohol, oleyl alcohol, octyldodecanol, oleic acid, isostearic acid and/or stearic acid.

(12) The present inventive medical skin external preparation according to any of the items 1 to 11, wherein an addition amount of the alcohol is in a range of 0.1 to 40% by weight.

(13) The present inventive medical skin external preparation according to any of the items 1 to 11, wherein an addition amount of the fatty acid is in a range of 0.1 to 40% by weight.

BRIEF DESCRIPTION OF THE DRAWINGS

FIG. 1 shows the skin absorbability of a Compound A according to a present inventive medical skin external preparation. The ordinate represents the cumulative permeation amount through skin (ng/cm$^2$) of the Compound A, and the abscissa represents time. The symbol * represents Cream 3, ■ represents Cream 13, ▲ represents Cream 14, ♦ represents Cream 15, □ represents Cream 16, and ● represents Cream 17.

MODE FOR CARRYING OUT THE INVENTION

A Compound A is classified as a quinolone synthetic antibacterial compound, and exhibits a broad antibacterial spectrum and strong antibacterial activity against Gram positive bacteria, Gram negative bacteria, anaerobic bacteria, chlamydia and drug resistant Gram positive bacteria by inhibiting DNA gyrase and topoisomerase IV involved in bacterial DNA replication.

Pharmaceutically acceptable salts of the Compound A may include commonly known salts for a basic group such as amino group or an acidic group such as hydroxyl group or carboxyl group.

Examples of the salts for a basic group may include salts with mineral acids such as hydrochloric acid, hydrobromic acid or sulfuric acid; salts with organic carboxylic acids such as tartaric acid, formic acid, fumaric acid, maleic acid, malic acid and citric acid; and salts with sulfonic acids such as methanesulfonic acid, benzenesulfonic acid, p-toluenesulfonic acid, mesitylenesulfonic acid and naphthalenesulfonic acid.

Examples of the salts for an acidic group may include salts with alkali metals such as sodium and potassium; salts with alkaline earth metals such as calcium and magnesium; ammonium salt; and salts with amino acids such as lysine, arginine and ornithine, and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-efenamine and N,N'-dibenzylethylenediamine.

The content of the compound A and/or the pharmaceutically acceptable salt thereof is not particularly limited as long as it exerts a therapeutic effect, but for example, it is suitably in the range of 0.01 to 20% by weight, preferably in the range of 0.1 to 5% by weight in a preparation.

Because the compound A is stable under alkaline conditions, the optimum pH of the present inventive medical skin external preparation is in the range of 9 to 13. The pH can be measured according to a commonly used method. The method is not particularly limited, but for example, the pH can be measured by adding purified water to a preparation for about 10 times dilution, followed by heating, then dissolving and mixing the preparation, followed by centrifugation, and collecting the lower part.

The alcohol and/or fatty acid according to the present invention has 12 or more carbon atoms, suitably 16 to 22 carbon atoms, preferably 18 carbon atoms. In addition, the alcohol and/or fatty acid according to the present invention is preferably those having an unsaturated carbon bond and/or a branched chain. One kind or two or more kinds of them may be used.

The alcohol according to the present invention is not particularly limited as long as it is pharmaceutically acceptable, but examples thereof may include the followings.
  Alcohol having 12 carbon atoms: lauryl alcohol
  Alcohol having 13 carbon atoms: tridecyl alcohol
  Alcohol having 14 carbon atoms: myristyl alcohol
  Alcohol having 15 carbon atoms: pentadecyl alcohol
  Alcohol having 16 carbon atoms: cetanol (cetyl alcohol, palmityl alcohol), hexyl decanol, palmitoleyl alcohol
  Alcohol having 17 carbon atoms: 1-heptadecanol
  Alcohol having 18 carbon atoms: stearyl alcohol, isostearyl alcohol, oleyl alcohol, elaidyl alcohol, linoleyl alcohol, elaidolinoleyl alcohol, linolenyl alcohol, elaidolinolenyl alcohol, ricinoleyl alcohol
  Alcohol having 19 carbon atoms: chimyl alcohol (glyceryl monocetyl ether), nonadecyl alcohol
  Alcohol having 20 carbon atoms: octyldodecanol, arachidyl alcohol
  Alcohol having 21 carbon atoms: batyl alcohol (glyceryl monostearyl ether), selachyl alcohol (monooleyl glyceryl ether), heneicosanol
  Alcohol having 22 carbon atoms: behenyl alcohol, erucyl alcohol
  Alcohol having 24 carbon atoms: decyltetradecanol, lignoceryl alcohol
  Alcohol having 26 carbon atoms: ceryl alcohol
  Alcohol having 27 carbon atoms: cholesterol (cholesterin), 1-heptacosanol
  Alcohol having 28 carbon atoms: montanyl alcohol
  Alcohol having 29 carbon atoms: sitosterol (sitosterin), 1-nonacosanol
  Alcohol having 30 carbon atoms: myricyl alcohol
  Alcohol having 32 carbon atoms: 1-dotriacontanol
  Alcohol having 34 carbon atoms: geddyl alcohol Furthermore, for example, also included are alcohols obtained by mixing plural alcohols, such as cetostearyl alcohol in which stearyl alcohol is mixed with cetanol. Examples of such alcohols include phytosterol (phytosterin), lanolin alcohol and hydrogenated lanolin alcohol.

The content of alcohol in the present inventive medical skin external preparation is suitably in the range of 0.1 to 40% by weight, preferably in the range of 0.5 to 20% by weight, more preferably in the range of 1 to 10% by weight.

The alcohol according to the present invention is suitably lauryl alcohol, hexyldecanol, isostearyl alcohol, oleyl alcohol or octyldodecanol, preferably isostearyl alcohol, oleyl alcohol or octyldodecanol, more preferably oleyl alcohol.

The fatty acid according to the present invention is not particularly limited as long as it is pharmaceutically acceptable, but examples thereof may include the followings.
  Fatty acid having 12 carbon atoms: lauric acid
  Fatty acid having 14 carbon atoms: myristic acid
  Fatty acid having 15 carbon atoms: pentadecylic acid
  Fatty acid having 16 carbon atoms: palmitic acid, palmitoleic acid
  Fatty acid having 17 carbon atoms: margaric acid
  Fatty acid having 18 carbon atoms: stearic acid, isostearic acid, oleic acid, linoleic acid, vaccenic acid, linolenic acid, eleostearic acid
  Fatty acid having 20 carbon atoms: arachidic acid, 8,11-eicosadienoic acid, mead acid, arachidonic acid
  Fatty acid having 22 carbon atoms: behenic acid
  Fatty acid having 24 carbon atoms: lignoceric acid, nervonic acid
  Fatty acid having 25 carbon atoms: pentacosanoic acid
  Fatty acid having 26 carbon atoms: cerotic acid
  Fatty acid having 28 carbon atoms: montanic acid
  Fatty acid having 30 carbon atoms: melissic acid The content of the fatty acid in the present inventive medical skin external preparation is suitably in the range of 0.1 to 40% by weight, preferably in the range of 0.5 to 20% by weight, more preferably in the range of 1 to 10% by weight, still more preferably in the range of 1 to 5% by weight.

The content of the alcohol and fatty acid in the present inventive medical skin external preparation is suitably in the range of 0.1 to 40% by weight, preferably in the range of 0.5 to 20% by weight, more preferably in the range of 1 to 10% by weight.

The fatty acid according to the present invention is suitably myristic acid, palmitic acid, stearic acid, oleic acid, isostearic acid or behenic acid, preferably stearic acid, oleic acid or isostearic acid, more preferably stearic acid.

A "medical skin external preparation" according to the present inventive medical skin external preparation means a formulation to be applied to human skin for medical use, and the medical skin external preparation is not particular limitation as long as it is pharmaceutically acceptable, but examples thereof may include an ointment, cream, lotion, gel or foam. Among them, an ointment or cream is particularly preferable.

An ointment is generally defined as a semi-solid formulation that will be applied to the skin, in which an active ingredient is dissolved or dispersed in a base, and can be classified into an oleaginous ointment and a water-soluble ointment. The oleaginous ointment may further be classified into a dispersion type in which an active ingredient is crystalline and is dispersed in a base, a liquid droplet dispersion type in which an active ingredient is dissolved in a dissolving agent for dispersion in a base, and a soluble type in which an active ingredient is dissolved in a base without requiring a dissolving agent.

A cream is generally defined as a semi-solid formulation that will be applied to the skin, which is emulsified in an oil-in-water or water-in-oil form.

The base to be used in the present inventive medical skin external preparation is not particularly limited as long as it is pharmaceutically acceptable, but examples thereof include oils and fats, waxes, hydrocarbons such as paraffin, or water. One kind or two or more kinds of them may be used.

The oils and fats are not particularly limited, but examples thereof include vegetable oils or squalane. One kind or two or more kinds of them may be used.

The waxes are not particularly limited, but examples thereof include beeswax, white beeswax or lanolin. One kind or two or more kinds of them may be used.

The paraffins are hydrocarbons having a chain length of C5 to C60, which have chain length peaks (measured by gas chromatography) at C14-16, C18-22, C20-22, C20-26, C28-40 and C40-44. Examples thereof include white petrolatum, yellow petrolatum, white soft paraffin, liquid paraffin or light liquid paraffin. One kind or two or more kinds of them may be used.

From the medical skin external preparation, a degradation product of the active ingredient may be generated due to time course, effect of, for example, light, heat, pH or water, or chemical reaction with a container or closure. Because the effectiveness and safety of the degradation product are unknown, taking Impurities in New Drug Products (ICH Q3B (R2), notification dated Jun. 24, 2003) into consideration, the degradation product is required to be suppressed to 0.5% or less with respect to the content of the active ingredient.

It has been found that when a medical skin external preparation containing the Compound A is prepared, the Compound A is decomposed. As a result of intensive studies, it has been found that this is because of peroxide in the alcohol and/or fatty acid added to the medical skin external preparation, so that controlling the peroxide value makes it possible to suppress the degradation product to 0.5% or less with respect to the content of the Compound A.

The degradation product of the Compound A was a compound (1-cyclopropyl-3-hydroxy-8-methyl-7-(5-methyl-6-(methylamino)pyridin-3-yl)quinolin-4(1H)-one) as represented by the following formula.

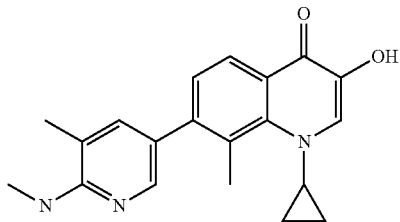

[Formula 1]

In order to suppress the degradation product to 0.5% or less with respect to the content of the Compound A, it is desirable that the peroxide value of the alcohol and/or fatty acid to be added to the present inventive medical skin external preparation be 120 meq/kg or less. When the peroxide value of the alcohol and/or fatty acid to be added to the present inventive medical skin external preparation is 40 meq/kg or less, the degradation product can be suppressed to 0.2% or less with respect to the content of the compound A, so that the stability can be further improved.

The content of the degradation product may be measured by a method commonly used by those skilled in the art, for example, high performance liquid chromatography.

The peroxide value may be measured by a commonly used method. The peroxide value is expressed as an amount of iodine molecules released from reaction of a sample with potassium iodide in the number of milliequivalent (meq) per kg of the sample. The amount of produced iodine molecules is determined by oxidation-reduction titration with sodium thiosulfate, for which titration starch is used to utilize iodo-starch reaction. Iodine molecules react with starch to give bluish purple color, but as sodium thiosulfate is added, iodine molecules are reduced and released from starch, resulting in a lighter color. The point at which the color has disappeared is the end point of titration.

In order to adjust the pH to 9 to 13, a pH adjusting agent may be added to the present inventive medical skin external preparation.

Such a pH adjusting agent is not particularly limited as long as it is a compound having a buffering capacity, but examples thereof include metal hydroxides such as potassium hydroxide, lithium hydroxide and sodium hydroxide; hydroxy lower alkyl amines such as monoethanolamine, monoisopropanolamine, diethanolamine, diisopropanolamine, triethanolamine, triisopropanolamine and 2-amino-2-methyl-1,3-propanediol; weak acid metal salts such as sodium bicarbonate, sodium citrate, sodium lactate, disodium hydrogen phosphate and sodium tartrate. One kind or two or more kinds of them may be used.

Furthermore, the addition amount of the pH adjusting agent is not particularly limited as long as the pH of the present inventive medical skin external preparation can be adjusted to 9 to 13, but it is suitably in the range of 0.1 to 20% by weight, preferably in the range of 0.1 to 10% by weight, more preferably in the range of 0.1 to 5% by weight.

A preservative (antiseptic) may be further added to the present inventive medical skin external preparation. The preservative is not particularly limited, but examples thereof include sodium edetate hydrate, tetrasodium edetate, sodium dehydroacetate, sorbic acid, potassium sorbate, phenoxyethanol, sodium benzoate, methyl parahydroxybenzoate, ethyl parahydroxybenzoate, propyl parahydroxybenzoate, thymol, benzalkonium chloride or dried sodium sulfite. One kind or two or more kinds of them may be used.

A stabilizer (including an antioxidant) may be further added to the present inventive medical skin external preparation. The stabilizer is not particularly limited, but examples thereof include ascorbic acid and derivatives thereof, sodium edetate, sodium thiosulfate, sodium sulfite, sodium pyrosulfite, sodium nitrite or dibutylhydroxytoluene. One kind or two or more kinds of them may be used.

An ultraviolet absorber may be further added to the present inventive medical skin external preparation. The ultraviolet absorber is not particularly limited, but examples thereof include paraaminobenzoic acid, phenyl salicylate, isopropyl paramethoxycinnamate, octyl paramethoxycinnamate or 2,4-dihydroxybenzophenone. One kind or two or more kinds of them may be used.

A solubilizer (solvent) for active ingredient may further be added to the present inventive medical skin external preparation. The solubilizer for active ingredient is not particularly limited, but examples thereof include 1,2,6-hexanetriol, crotamiton, squalane, silicone oil, isostearyl palmitate, cetyl 2-ethylhexanoate, polypropylene glycol 2000, tri(caprylic acid/capric acid) glycerin, hexadecyl isostearate, liquid paraffin, isopropyl myristate, octyldodecanol, isostearyl alcohol, middle chain fatty acid triglyceride, oleyl alcohol, hexyl decanol, glyceryl triisooctanoate, diisopropyl sebacate, lauryl alcohol, castor oil, isostearic acid, diethyl sebacate, diisopropyl adipate, water, benzyl alcohol, triacetin, propylene carbonate, sorbitan monolaurate, 2-ethyl-1,3-hexanediol, ethylene glycol salicylate, dipropylene glycol, ethanol, macrogol 400, 1,3-butylene glycol, propylene glycol, lactic acid and D-sorbitol or glycerin. One kind or two or more kinds of them may be used.

A wetting agent may be further added to the present inventive medical skin external preparation. The wetting agent is not particularly limited, but examples thereof include 1,3-butylene glycol, glycerin, propylene glycol and dipropylene glycol. One kind or two or more kinds of them may be used.

An emulsifier may be further added to the present inventive medical skin external preparation. The emulsifier is not particularly limited, but includes cetyl trimethyl ammonium chloride, lauryl dimethyl benzyl ammonium chloride, tetrabutylammonium chloride, dioctadecyldimethylammonium chloride, sodium alkylbenzenesulfonate, sodium dodecyl sulfate, coconut alcohol sodium ethoxysulfate, sodium α-olefin sulfonate, emulsified cetostearyl alcohol, polyoxyethylene alkyl ether, polyoxyethylene alkylphenol ether, polyoxyethylene hydrogenated castor oil, polyoxyl stearate, glycerin fatty acid ester, diglycerin fatty acid ester, N-alkyl-N,N-dimethylammonium betaine or imidazoline type amphoteric surfactant. One kind or two or more kinds of them may be used.

An emulsion stabilizer may be further added to the present inventive medical skin external preparation. The emulsion stabilizer is not particularly limited, but examples thereof include L-arginine, glycine or sodium N-acyl-L-glutamate. One kind or two or more kinds of them may be used.

A thickener (including a gelling agent) may be further added to the present inventive medical skin external preparation. The thickener is not particularly limited, but examples thereof include sodium alginate, gelatin, carboxyvinyl polymer, sodium polyacrylate, methyl cellulose, glycerin monooleate, hydroxypropyl cellulose, hydroxypropyl methyl cellulose, hydroxyethyl cellulose or xanthan gum. One kind or two or more kinds of them may be used.

A foaming agent may be further added to the present inventive medical skin external preparation. The foaming agent is not particularly limited, but examples thereof include polyoxyethylene sorbitan monostearate, glyceryl stearate, polyoxyethylene hydrogenated castor oil, polyethylene glycol monostearate, sucrose lauric acid ester, polyoxyethylene stearyl ether, sodium laurate, arginine stearate or sodium lauryl sulfate. One kind or two or more kinds of them may be used.

The present inventive medical skin external preparation may further contain other additives commonly used in a skin external preparation.

The present inventive medical skin external preparation can be widely used for treatment and/or prevention of dermatological infection based on the antibacterial action of the active ingredient.

The dermatological infection for which the present inventive medical skin external preparation may be used is not particularly limited as long as it is a disease of which bacterial infection is one of the etiologies, but examples thereof may include uncomplicated skin and soft tissue infection, complicated skin and soft tissue infection or acne accompanied by suppurative inflammation.

Examples of uncomplicated skin and soft tissue infection may include superficial skin infection or deep skin infection. Among them, superficial skin infection is particularly preferable.

Superficial skin infection may be divided into appendage-associated infection and non-appendage-associated infection.

Examples of appendage-associated infection may include folliculitis, sycosis or purulent periporitis.

Examples of non-appendage-associated infection may include infectious impetigo.

Complicated skin and soft tissue infection may also be divided into appendage-associated infection and non-appendage-associated infection.

Examples of appendage-associated infection may include furuncle, furunculosis or carbuncle.

Examples of non-appendage-associated infection may include cellulitis, erysipelas, lymphangitis or lymphadenitis.

Complicated skin and soft tissue infection may be divided into chronic pyoderma and secondary skin infection.

Examples of chronic pyoderma may include infectious atheroma and hidradenitis suppurativa.

Examples of secondary skin infection may include secondary infections such as skin ulcer.

Examples of acne accompanied by suppurative inflammation may include acne vulgaris, acne neonatorum or acne conglobata.

The present inventive medical skin external preparation causes less irritation to the skin, and is particularly useful for, among these dermatological infections, diseases and symptoms accompanied by blister or erosion. The diseases accompanied by blister or erosion are not limited, but examples thereof may include infectious impetigo.

A method for producing the present inventive medical skin external preparation is not particularly limited, but those skilled in the art can produce it by a generally usable method.

EXAMPLES

Hereinafter, more detailed description is made of the present invention with reference to Formulation Examples and Test Examples, but the present invention is not limited to the scope described in the Examples.

Formulation Examples 1 to 17

Preparation of Medical Skin External Preparation

Based on the compositions shown in Tables 1 to 3, each ingredient was weighed. Water and a pH adjusting agent were added to a Compound A, followed by stirring, to yield a main drug phase. Separately, a pH adjusting agent was added to water, followed by stirring, to yield a pH adjusting phase. An oil phase containing white petrolatum, alcohol and/or fatty acid was warmed to 70 to 80° C. for dissolution. The main drug phase and the pH adjusting phase were added to the oil phase, and the mixture was stirred using an emulsifying machine (manufactured by PRIMIX Corporation) to yield each cream of Examples.

TABLE 1

| Composition (% by weight) | Formulation Example 1 Cream 1 | Formulation Example 2 Cream 2 | Formulation Example 3 Cream 3 | Formulation Example 4 Cream 4 | Formulation Example 5 Cream 5 | Formulation Example 6 Cream 6 |
|---|---|---|---|---|---|---|
| Compound A | 2 | 2 | 2 | 2 | 2 | 2 |
| pH adjusting agent | Appropriate amount | Appropriate amount | Appropriate amount | Appropriate amount | Appropriate amount | Appropriate amount |
| Oleyl alcohol | 5 | 5 | 5 | 5 | 5 | 5 |
| White petrolatum | Balance | Balance | Balance | Balance | Balance | Balance |
| Purified water | 15 | 15 | 15 | 15 | 15 | 15 |
| pH | 10.78 | 10.77 | 10.97 | 10.75 | 10.73 | 10.71 |

TABLE 2

| Composition (% by weight) | Formulation Example 7 Cream 7 | Formulation Example 8 Cream 8 | Formulation Example 9 Cream 9 | Formulation Example 10 Cream 10 | Formulation Example 11 Cream 11 | Formulation Example 12 Cream 12 |
|---|---|---|---|---|---|---|
| Compound A | 2 | 2 | 2 | 2 | 2 | 2 |
| pH adjusting agent | Appropriate amount | Appropriate amount | Appropriate amount | Appropriate amount | Appropriate amount | Appropriate amount |
| Oleyl alcohol | 5 | 5 | 5 | 5 | 5 | 5 |
| Stearic acid | — | 2 | — | 2 | 2 | — |
| White petrolatum | Balance | Balance | Balance | Balance | Balance | Balance |
| Purified water | 15 | 15 | 15 | 15 | 15 | 15 |
| pH | 10.78 | 10.76 | 10.59 | 10.56 | 10.58 | 10.91 |

TABLE 3

| Composition (% by weight) | Formulation Example 13 Cream 13 | Formulation Example 14 Cream 14 | Formulation Example 15 Cream 15 | Formulation Example 16 Cream 16 | Formulation Example 17 Cream 17 |
|---|---|---|---|---|---|
| Compound A | 2 | 2 | 2 | 2 | 2 |
| pH adjusting agent | Appropriate amount | Appropriate amount | Appropriate amount | Appropriate amount | Appropriate amount |
| Octyldodecanol | 5 | — | — | — | — |
| Isostearyl alcohol | — | 3 | — | — | — |
| Lauryl alcohol | — | — | 3 | — | — |
| Oleic acid | — | — | — | 0.8 | — |
| Isostearic acid | — | — | — | — | 6 |
| White petrolatum | Balance | Balance | Balance | Balance | Balance |
| Purified water | 15 | 7.5 | 15 | 15 | 15 |
| pH | 10.97 | 10.88 | 10.85 | 10.83 | 10.97 |

Test Example 1

Evaluation of Skin Absorbability

A human skin section from which subcutaneous fat had been removed was attached to a Franz vertical permeation cell (manufactured by Hanson Research Corporation), and each of Creams 3 and 13 to 17 was applied on the section so as to be about 20 mg per 1.77 cm$^2$, followed by perfusion with a receptor solution. Then, using LC/MS/MS (liquid chromatograph (LC): manufactured by Shimadzu Corporation, tandem mass spectrometer (MS/MS): manufactured by AB Sciex), the cumulative permeation amount through human skin was measured over time. The number of human skin sections used per formulation was 6 to 8. The results are shown in FIG. 1.

As is apparent from FIG. 1, by the medical skin external preparation according to any of Creams 3 and 13 to 17, good skin absorbability was recognized.

Test Example 2

Examination for Produced Amount of Degradation Product

The produced amount of the degradation product (1-cyclopropyl-3-hydroxy-8-methyl-7-(5-methyl-6-(methylamino)pyridin-3-yl)quinolin-4(1H)-one) in each of the medical skin external preparations shown in Tables 1 to 3 was measured using high performance liquid chromatography. Measurement of the degradation product was carried out immediately after preparation of the formulation.

The peroxide value and the amount of the degradation product were examined for the medical skin external preparations shown in Tables 1 to 3. As a result, as is apparent from Tables 4 to 6, it was found that when the peroxide value was set to 120 meq/kg or less, the production of the degradation product could be suppressed to 0.5% or less with respect to the content of the Compound A, and when the peroxide value was set to 40 meq/kg or less, the production of the degradation product could be suppressed to 0.2% or less with respect to the content of the Compound A.

TABLE 4

| Composition (% by weight) | Formulation Example 1 Cream 1 | Formulation Example 2 Cream 2 | Formulation Example 3 Cream 3 | Formulation Example 4 Cream 4 | Formulation Example 5 Cream 5 | Formulation Example 6 Cream 6 |
|---|---|---|---|---|---|---|
| Degradation product (amount with respect to compound A (%)) | Less than 0.05 | Less than 0.05 | 0.06 | 0.06 | 0.07 | 0.07 |
| Peroxide value (meq/kg) | 1.2 | 5.3 | 6.2 | 13.0 | 15.9 | 22.7 |

TABLE 5

| Composition (% by weight) | Formulation Example 7 Cream 7 | Formulation Example 8 Cream 8 | Formulation Example 9 Cream 9 | Formulation Example 10 Cream 10 | Formulation Example 11 Cream 11 | Formulation Example 12 Cream 12 |
|---|---|---|---|---|---|---|
| Degradation product (amount with respect to compound A (%)) | 0.20 | 0.41 | 0.38 | 0.64 | 0.75 | 2.67 |
| Peroxide value (meq/kg) | 43.7 | 88.0 | 100.1 | 133.9 | 169.2 | 275.1 |

TABLE 6

| Composition (% by weight) | Formulation Example 13 Cream 13 | Formulation Example 14 Cream 14 | Formulation Example 15 Cream 15 | Formulation Example 16 Cream 16 | Formulation Example 17 Cream 17 |
|---|---|---|---|---|---|
| Degradation product (amount with respect to compound A (%)) | 0.11 | Less than 0.05 | Less than 0.05 | 0.05 | Less than 0.05 |
| Peroxide value (meq/kg) | 27.88 | 0.00 | 0.00 | 0.00 | 0.73 |

The invention claimed is:

1. A medical skin external preparation consisting essentially of:
    about 2 wt % of 1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof as an active ingredient;
    about 2 wt % of stearic acid;
    about 5 wt % of oleyl alcohol;
    about 15 wt % of water;
    one or more pH adjusting agents; and
    white petrolatum, wherein the medical skin external preparation is a cream preparation having a pH of 9 to 13, and wherein the peroxide value is 120 meq/kg or less, wherein each wt % is with respect to the total weight of the preparation.

2. The medical skin external preparation according to claim 1, consisting of:
    1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof;
    stearic acid;
    oleyl alcohol;
    water;
    the one or more pH adjusting agents; and
    white petrolatum.

3. The medical skin external preparation according to claim 1, wherein the content of a degradation product of the active ingredient is 0.5% or less with respect to the active ingredient.

4. The medical skin external preparation according to claim 1, wherein the degradation product of the active ingredient is 1-cyclopropyl-3-hydroxy-8-methyl-7-(5-methyl-6-(methylamino)pyridin-3-yl)quinolin-4(1H)-one.

5. The medical skin external preparation according to claim 1, wherein the peroxide value is 40 meq/kg or less.

* * * * *